United States Patent [19]

Morrow

[11] Patent Number: 5,172,264
[45] Date of Patent: Dec. 15, 1992

[54] METHOD AND APPARATUS FOR COMBINING CONTINUOUS WAVE LASER WITH TEA PULSED LASER

[75] Inventor: Clifford E. Morrow, North Kingstown, R.I.

[73] Assignee: Surgilase, Inc., Warwick, R.I.

[21] Appl. No.: 658,920

[22] Filed: Feb. 21, 1991

[51] Int. Cl.$^5$ .................. A61B 17/36; A61N 5/06; H01S 3/23
[52] U.S. Cl. .................. 359/349; 606/3; 606/11; 372/97
[58] Field of Search .................. 330/4.3; 606/11, 3, 606/13; 372/97; 359/349; 219/121.76

[56] References Cited

U.S. PATENT DOCUMENTS

| | | | |
|---|---|---|---|
| 3,769,963 | 11/1973 | Goldman et al. | 128/2 |
| 4,069,823 | 1/1978 | Isakov et al. | 606/11 |
| 4,469,098 | 9/1984 | Davi | 219/121 |
| 4,503,854 | 3/1985 | Jako | 606/11 |
| 4,550,240 | 10/1985 | Toida et al. | 219/121 LS |
| 4,573,465 | 3/1986 | Sugiyama et al. | 372/23 |
| 4,573,467 | 3/1986 | Rich et al. | 606/11 |
| 4,601,037 | 7/1986 | McDonald | 372/25 |
| 4,672,969 | 6/1987 | Dew | 606/11 |
| 4,940,411 | 7/1990 | Vassiliadis et al. | 606/16 |
| 4,982,166 | 1/1991 | Morrow | 330/4.3 |
| 5,002,051 | 3/1991 | Dew et al. | 128/395 |
| 5,062,842 | 11/1991 | Tiffany | 606/3 |
| 5,067,951 | 11/1991 | Greve | 606/604 |
| 5,084,043 | 1/1992 | Hartzmann et al. | 606/3 |

FOREIGN PATENT DOCUMENTS 8705794  10/1987  World Int. Prop. O. ............ 606/11

Primary Examiner—Nelson Moskowitz
Attorney, Agent, or Firm—Kenyon & Kenyon

[57] ABSTRACT

An apparatus comprising a continuous wave (CW) laser and a transverse electrode atmospheric (TEA) pulsed laser, the continuous wave laser and transverse electrode atmospheric pulsed laser each producing laser beams, the laser beams from each of the lasers being provided to an optical mixer for combing the two laser beams into an output beam. The output beam can be either laser beam individually, or a combined coaxial beam wherein the CW laser beam and TEA pulsed laser beam are superimposed on each other. Preferably, the two lasers are $CO_2$ lasers. The CW laser can also be operated in a pulsed mode. The device is particularly useful for medical and surgical treatment and provides effects not possible before.

19 Claims, 3 Drawing Sheets

THE COMBINATION OF $CO_2$ CONTINUOUS WAVE LASER WITH A TEA PULSED LASER FOR APPLICATIONS IN LASER SURGERY.

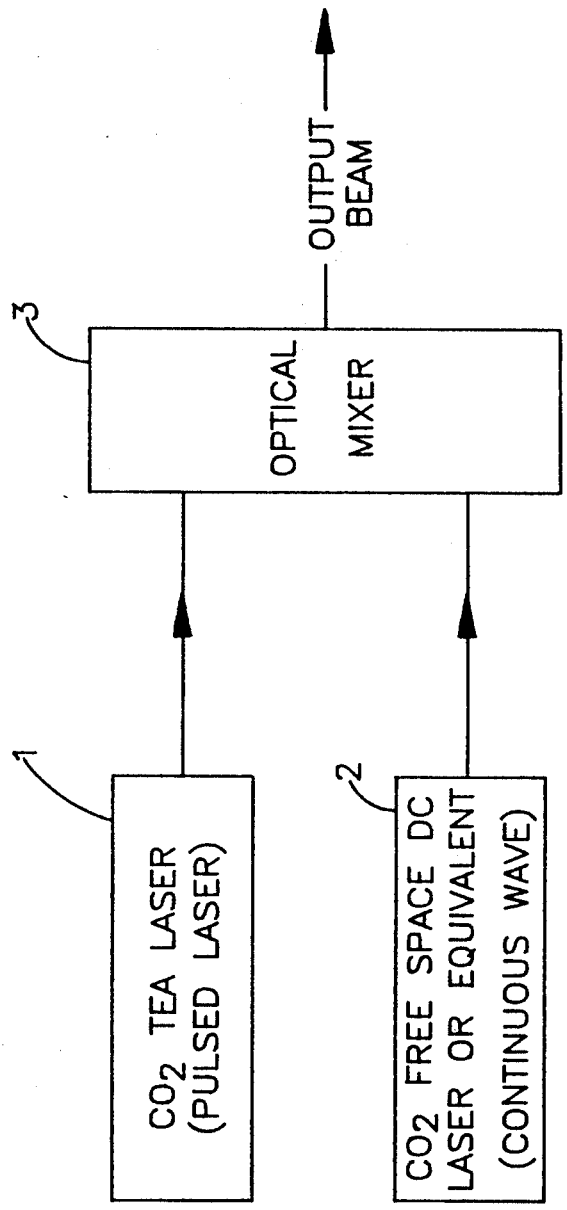

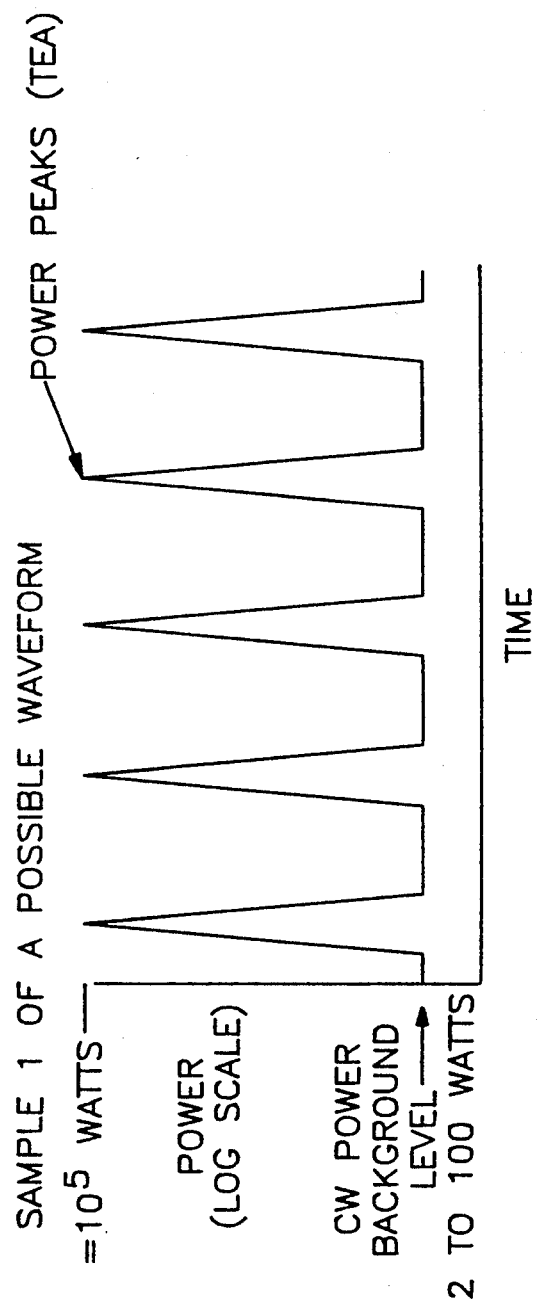

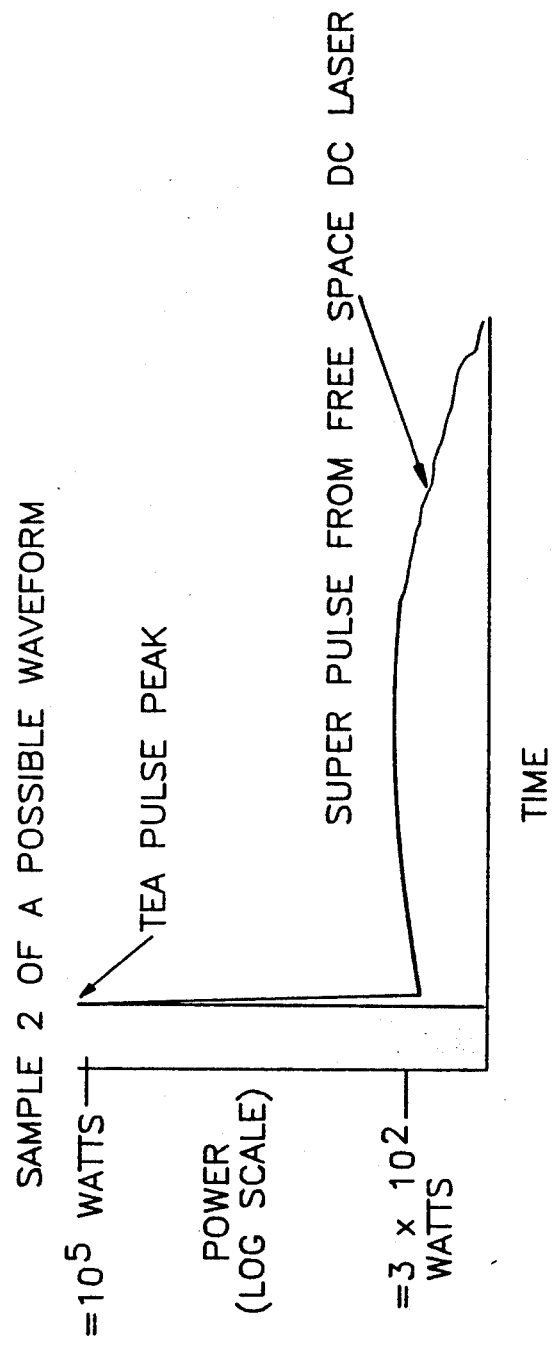

1

METHOD AND APPARATUS FOR COMBINING CONTINUOUS WAVE LASER WITH TEA PULSED LASER

BACKGROUND OF THE INVENTION

The present invention relates to lasers, and in particular, to a novel apparatus for combining the laser beams from a CW (continuous wave) laser with a TEA (Transverse Electrode Atmospheric) laser, and more particularly to such a laser device which has application in the medical and surgical fields.

The utility of the conventional continuous wave laser, for example, a $CO_2$ laser, in surgery, has for years been enhanced by the ability of these lasers to produce a limited variety of pulsed waveforms, most often called "Super Pulse". These pulsed waveforms are really "gain switched" outputs that result from very brief (~100us to 600us) applications of pump power at levels somewhat above the normal limits of the laser operating in CW mode. The peak power and energy of these pulses in surgery can provide enhanced cutting effects for certain procedures. For example, the pulsing waveform minimizes the damage to adjacent tissue since the heat of the laser does not have time to conduct far from the site of impact during the brief moment of exposure. This is not true of a CW laser beam. The difference is a charring effect on the edge of a CW cut and a greater region of laterally affected tissue, caused by the continuous nature of the CW laser output.

The brief high bursts of energy have the effect of exploding away each tiny volume of tissue rather than slowly vaporizing, burning, or boiling the tissue away.

Unfortunately, there are limits to the magnitude of the energy and peak power that can be achieved when running a CW laser in the gain switched moded. With much greater peak power and energy, many new procedures are possible, i.e., bone cutting and the removal of cements that attach artificial joints to bones that need replacement, dental applications, and other instances where greater peak power is required.

SUMMARY OF THE INVENTION

It is an object of the present invention to provide a novel method and apparatus for achieving greater peak laser power in a pulsed mode than has heretofore been known.

It is furthermore an object of the present invention to provide such a method and apparatus which provides laser power in pulsed format so as to minimize burning, charring, boiling or searing effects heretofore known when using both continuous wave lasers in normal CW mode and gain switched CW lasers.

It is furthermore an object of the invention to achieve greater peak powers than such CW mode lasers operated in the gain switched mode have heretofore been capable of attaining.

It is yet still a further object of the invention to provide a method and apparatus for providing laser energy in both CW and pulsed format, either individually or simultaneously.

It is yet still a further object to provide such a laser device which has application in the medical and surgical field, and particularly which is useful in providing higher power levels to areas of medical treatment without causing burning, boiling, or charring effects.

It is yet still a further object to provide a laser device which is capable of providing greater energy in a shorter pulse, thus allowing new medical procedures to be performed which have heretofore not been possible.

The above and other objects of the present invention are achieved by an apparatus comprising a continuous wave laser (CW) and a transverse electrode atmospheric (TEA) pulsed laser, the continuous wave laser and transverse electrode atmospheric pulsed laser each producing a laser beam, the laser beams from each of the lasers being provided to means for combining the two laser beams into an output beam, the output beam comprising a laser beam having at least one of a continuous wave and a pulsed mode.

The output beam can comprise either of the two laser beams individually or may comprise both CW and pulsed laser beams superimposed on each other, thereby providing new and improved effects in surgical and medical laser treatment.

Preferably both the CW and TEA lasers comprise $CO_2$ lasers.

Methods for providing medical treatment in accordance with the invention are also disclosed.

BRIEF DESCRIPTION OF THE DRAWINGS

The invention will be described in greater detail in the following detailed description with reference to the drawings in which:

FIG. 1 shows the basic arrangement of the apparatus according to the present invention;

FIG. 2 shows a sample waveform generated by the apparatus according to the present invention; and FIG. 3 shows another sample waveform generated by the apparatus according to the present invention.

DETAILED DESCRIPTION

With reference now to the drawings, to achieve the required higher peak power and pulsed energy, a Transverse Electrode Atmospheric (TEA) laser may be utilized. The TEA laser is shown at 1 in FIG. 1. With such a laser, designed to produce equivalent average output power of a CW laser, the peak powers would be from 1000 to 4000 times higher and the pulse energies would be about 10 times higher. See, for example, the output waveform shown in FIG. 2, which shows power peaks of the TEA laser superimposed upon a CW power background level. Since the TEA laser cannot operate in CW mode, however, and it is important also to be able to provide CW mode power, a CW laser 2 is also provided, with the two types of lasers being combined in a common package and their output beams combined coaxially by a mixing device 3, preferably the optical mixing device shown in U.S. Pat. No. 4,982,166 to Morrow. Alternatively, other mixing means, for example, a series arrangement, can be used. The disclosure of U.S. Pat. No. 4,982,166 is hereby incorporated by reference. The outputs of the two lasers can then be combined to generate new waveforms not possible before, i.e., CW background power with superimposed high power peaks (FIG. 2) or high power peaks of low average power in the background with heavy CW energy deposition superimposed. Alternatively, the duration and shape of the output pulse can be controlled by timing the pulse output of each type laser 1 and 2 to generate combined pulsed waveforms as in, for example, FIG. 3, where the CW laser is operated in the gain switched or pulsed mode. In FIG. 3, a super pulse from a free space $CO_2$ D.C. laser is shown following the TEA pulse peak. Because of the vastly different time scale, the super pulse (typically pulse widths of approx. 200 usecs) shown in FIG. 3 is stretched out in comparison to the TEA pulse (typically pulse widths of approx. 50 nsecs. The two laser beams superimposed provide the best effects of each laser at the same time and make possible new tissue effects not possible before.

The two lasers can also be operated individually, so that the output beam from mixer 3 may be either a CW beam or a pulsed beam alone, as necessary for the particular application. Thus, when only pulsed power is needed, the CW laser would be disabled. If only CW power is required, the TEA laser would be disabled. When operated simultaneously, however, the combined laser beam having the characteristics of both types of laser offers advantages not possible before. For example, the laser according to the invention can be used in applications requiring the constant cutting power provided by a $CO_2$ CW laser but yet which requires greater peak powers (bone or dental cutting) without producing the deleterious burning effects of known high power CW lasers.

Additionally, as discussed, the CW laser can also be operated in the gain switched (and Q switched) pulse modes and be combined with the output of the TEA laser with variable timing. The variable timing can be achieved by both variable pulse widths and/or variable pulse timing. Q switching is another way of generating pulsed outputs where the gain of a lasing medium is allowed to build up to high levels while the "Q" of the cavity is spoiled by any of several means. When the Q is restored, the stored energy is released as a pulse of high power until the gain medium is depleted to its normal saturated CW levels.

Gain switching involves pulsing the pump power to the gain medium which allows the gain to build to high levels prior to the onset of lasing in a cavity of fixed "Q".

In the foregoing specification, the invention has been described with reference to a specific exemplary embodiment thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. An apparatus for surgery comprising a continuous wave (CW) carbon dioxide laser and a transverse electrode atmospheric (TEA) carbon dioxide pulsed laser, said continuous wave laser and said transverse electrode atmospheric pulsed laser each producing a laser beam, said laser beams from each of said lasers being provided to means for combining said two laser beams into an output beam, wherein said output beam comprises a laser beam having at least one of a continuous waveform and pulsed waveform or combination thereof.

2. The apparatus recited in claim 1, wherein said means for combining comprises means for combining said laser beams from said TEA laser and said CW laser into a combined coaxial laser beam.

3. The apparatus recited in claim 1, wherein the output beam comprises a continuous wave beam and a pulsed beam superimposed on each other.

4. The apparatus recited in claim 1, wherein one of said CW laser and said TEA laser can be disabled such that the laser beam from each laser can be delivered individually to a treatment area.

5. The apparatus recited in claim 1, wherein outputs from said two lasers are delivered simultaneously to a treatment area.

6. The apparatus recited in claim 1, wherein said CW laser is operated in a pulse mode.

7. The apparatus recited in claim 6, wherein said pulse mode comprises one of a gain switched mode and Q switched mode.

8. The apparatus recited in claim 6, wherein pulse widths of at least one of the TEA laser and the CW laser operated in pulse mode are variable.

9. The apparatus recited in claim 7 wherein the timing of pulses from at least one of the TEA and CW laser are variable.

10. A method for medical treatment comprising providing a continuous wave (CW) carbon dioxide laser and a transverse electrode atmospheric (TEA) carbon dioxide pulsed laser, generating laser beams from said continuous wave laser and said transverse electrode atmospheric pulsed laser, combining said two laser beams into an output beam, and providing the output beam to an area of medical treatment.

11. The method recited in claim 10, wherein said step of combining comprises combining each of said laser beams from said TEA laser and said CW laser into a combined coaxial beam.

12. The method recited in claim 10, wherein said step of combining comprises superimposing said CW and pulsed laser beams on each other.

13. The method recited in claim 10, further comprising disabling one of said CW laser and TEA laser such that the laser beam from each laser can be delivered individually to a site of medical treatment.

14. The method recited in claim 10, further comprising delivering outputs from said two lasers simultaneously to a site of medical treatment.

15. The method recited in claim 10, further comprising the step of operating said CW laser in a pulse mode.

16. The method recited in claim 15, wherein said step of operating comprises operating the CW laser in one of a gain switched mode and a Q switched mode.

17. The method recited in claim 10, wherein the pulse widths of at least one of the TEA laser and CW laser operated in pulse mode are variable.

18. The method recited in claim 10, wherein the timing of pulses from at least one of the TEA and CW laser are variable.

19. The apparatus of claim 1, wherein the continuous wave laser is operated in a pulsed waveform and said output beam has a waveform comprising a super pulse following a TEA pulse peak or visa versa.

* * * * *